United States Patent
Koski et al.

(10) Patent No.: US 7,319,030 B2
(45) Date of Patent: Jan. 15, 2008

(54) **NON-SPORULATING *BACILLUS SUBTILIS* HAVING PARTS OF THE GENE ENCODING SIGMA G DELETED**

(75) Inventors: Pertti Koski, Helsinki (FI); Susanna Kääriäinen, Espoo (FI)

(73) Assignee: Ipsat Therapies Oy, Espoo (FI)

( * ) Notice: Subject to any disclaimer, the term of this patent is extended or adjusted under 35 U.S.C. 154(b) by 431 days.

(21) Appl. No.: 10/494,411

(22) PCT Filed: Nov. 5, 2002

(86) PCT No.: PCT/FI02/00861

§ 371 (c)(1), (2), (4) Date: May 5, 2004

(87) PCT Pub. No.: WO03/040352

PCT Pub. Date: May 15, 2003

(65) Prior Publication Data

US 2005/0158843 A1    Jul. 21, 2005

(30) Foreign Application Priority Data

Nov. 6, 2001    (FI) .................................. 20012143

(51) Int. Cl.
*C12N 1/20* (2006.01)
*C12N 1/12* (2006.01)
*G01N 33/554* (2006.01)
*C12N 15/63* (2006.01)

(52) U.S. Cl. ............................. 435/252.31; 435/7.32; 435/252.1

(58) Field of Classification Search ..................... None
See application file for complete search history.

(56) References Cited

U.S. PATENT DOCUMENTS

2004/0248279 A1    12/2004    Sawada et al.

FOREIGN PATENT DOCUMENTS

WO    WO 9703185 A1    1/1997

OTHER PUBLICATIONS

Sambrook and Russell. Molecular Cloning: A Laboratory Manual. In vitro Amplification of DNA by the Polymerase Chain Reaction. vol. 2, Ch. 8, pp. 8.1-18.413. 2001.*
Saunders et al. Use of Chromosomal Integration in the Establishment and Expression of blaZ, a *Staphylococcus aureus* beta-lactamase Gene, in *Bacillus subtilis*. J. of Bacteriology, 157(3): 718-726. 1984.*
Pedraza-Reyes et al. Temporal Regulation and Forespore-Specific Expression of the Spore Photoproduct Lyase Gene by Sigma-G RNA Polymerase during *Bacillus subtilis* Sporulation. J. Bac. 176(13): 3983-3991. 1994.*
Biotechnology Letters, vol. 23, 2001, June-Hyung Kim et al., "Construction of spore mutants of Bacillus subtilis for the development as a host for foreign protein production," pp. 999-1004.

* cited by examiner

*Primary Examiner*—Joseph Woitach
*Assistant Examiner*—Michele K. Joike
(74) *Attorney, Agent, or Firm*—Crowell & Moring LLP (57) ABSTRACT

A non-sporulating *Bacillus subtilis* strain, a method for preparing it and its use as a production organism. A method for preparing a biologically prepared product with the non-sporulating bacterium is also disclosed.

5 Claims, 3 Drawing Sheets

```
                                                      SQ1-F->
                                     1603939 -TGCGTTAAACCGGATCACGTAA
↓
CGATTATGACAAAAGAAGAAATGATTTCTGCAGATAAATGTTTAATCGGTATCAGCACAA
     A----------------->
CAAAGCTGTCGGCAGATGGAGAGTTTGACGCGATTATTCATCCGAAAATGCTTTCGGGCA
AGGCTGTCAAACACGTTTCATAATGTTCGCAAATGTCCGTTACTTATCATACTCAAACGG
CGTGACATTTAGAAGGGAGAGGAAGATGAAAAAACTGAAATTACGGTTGACGCACCTCTG
GTATAAGCTGCTGATGAAACTTGGGCTGAAAAGTGATGAAGTCTATTACATAGGCGGGAG
TGAAGCCCTGCCGCCTCCATTATCTAAAGATGAGGAGCAGGTTTTGTTAATGAAGCTCCC
AAACGGCGATCAGGCGGCGCGCGCCATTCTAATTGAACGCAATTTGCGTCTGGTCGTATA
TATCGCCCGTAAATTTGAAAATACGGGAATTAATATAGAGGATTTAATCAGCATCGGTAC
CATCGGTCTAATCAAAGCTGTTAATACATTTAATCCAGAAAAGAAAATCAAGCTTGCTAC
CTATGCCTCCCGGTGTATAGAAAATGAAATCCTGATGTATTTAAGAAGAAATAACAAAAT
CCGTTCAGAGGTTTCCTTTGATGAACCGCTTAATATTGATTGGGACGGCAATGAGCTTTT
GCTTTCTGATGTGCTCGGCACTGACGATGAGCATCATCACTAAAGACATAGAAGCTAACGT
CGATAAAAAGCTTTTGAAAAAAGCGCTTGAACAGCTTAATGAGAGAGAAAAGCAAATCAT
                                                           SQ3-F->
GGAGCTGCGGTTTGGGCTTGTCGGTGAAGAAGAAAAAACCCAAAAGGATGTAGCGGATAT
GATGGGGATTTCTCAGTCTTATATTTCGCGGCTTGAGAAAAGAATTATAAAAAGGTTGAG
AAAAGAGTTCAACAAAATGGTGTAAAAAATTTTATGGTTAGAACCCCTTGATTTTACAGG
GATTTCCTGATTTCGACAGTTTTTCGGTCTGAGTGCAGTGCATATTTTTCCCACCCAAGG
                                       <-SQ2-R   1605025
                                              sigG
AGATACTTAACGTTGTACAGCAGCTCCTGTAGGGAGGGAAAAAAGTGTCGAGAAATAAAG
    C-------------------->    <----------------
TCGAAATCTGCGGGGTGGATACCCGGCAATAGTTACCCTTATTATCAAGATAAGAAAGAA
------------------B AAGGATTTTTCGCTACGCTCAAATCCTTTAAAAAAACACAAAAGACCACATTTTTTAATG
TGGTCTTTTATTCTTCAACTAAAGCACCCATTAGTTCAACAAACGAAAATTGGATAAAGT
GGGATATTTTTAAAATATATATTTATGTTACAGTAATATTGACTTTTAAAAAGGATTGA
TTCTAATGAAGAAAGCAGACAAGTAAGCCTCCTAAATTCACTTTAGATAAAAATTTAGGA
        cat
GGCATATCAAATGAACTTTAATAAAATTGATTTAGACAATTGGAAGAGAAAAGAGATATT
TAATCATTATTTGAACCAACAAACGACTTTTAGTATAACCACAGAAATTGATATTAGTGT
TTTATACCGAAACATAAAACAAGAAGGATATAAATTTTACCCTGCATTTATTTTCTTAGT
GACAAGGGTGATAAACTCAAATACAGCTTTTAGAACTGGTTACAATAGCGACGGAGAGTT
AGGTTATTGGGATAAGTTAGAGCCACTTTATACAATTTTTGATGGTGTATCTAAAACATT
CTCTGGTATTTGGACTCCTGTAAAGAATGACTTCAAAGAGTTTTATGATTTATACCTTTC
TGATGTAGAGAAATATAATGGTTCGGGGAAATTGTTTCCCAAAACACCTATACCTGAAAA
           SQ5-F->
TGCTTTTTCTCTTTCTATTATTCCATGGACTTCATTTACTGGGTTTAACTTAAATATCAA TAATAATAGTAATTACCTTCTACCCATTATTACAGCAGGAAAATTCATTAATAAAGGTAA
                       <- SQ4-R
TTCAATATATTTACCGCTATCTTTACAGGTACATCATTCTGTTTGTGATGGTTATCATGC
AGGATTGTTTATGAACTCTATTCAGGAGTTGTCAGATAGGCCTAATGACTGGCTTTTATA
                                                          *
ATATGAGATAATGCCGACTGTACTTTTTACAGTCGGCTTTCTAATGTCACTAACCTGCCC
    E--------------------------------->    <-
CGTTAGTTGAAGAAGGGAAATCTGCGGGGTGGATACCTCAAGCGCAGGTGTCCAGACTTG
--------------------D
AAAAAGCGGCTATCAAACAAATGAATAAAAATATTCATCAATAATGAAAAGCCTTTAAAA
                                      *END
CGATGTTGTTTTAAAGGCTTTTCTATTGATTATGGATGGTTTACGTTTTGGAAAAAGTAA
SQ6-F->
GGTATCCTAGTTCGTACAAAGTTTTATGAAAATTAAAACAATTATAAAAGGCAATAAAGA
GGAGGACCACGATGATTTTGCAGCTTGACAATGTCTCACTAAAACGGAATGGGAAATGGA
TACTGAAAGATATTCATTGGAAGGTGGAAGAAAAGGAAAATTGGGTGCTTTACGGCCTAA
ATGGCGCCGGGAAGACAGCGCTGTTAAATATGCTTTGCTCATATTATTTTCCAACATCAG
GCGAGATGCAGGTGCTCGGCCATGAATTTGGCAAAACAGAGCTTGGGGAAAAGCTCAGAC
GTAAAATTGGCCTCGTCTCAGCAGCTCTTCAGCAAAAATTGTATCCGGCAGATTCAGCTT
TTGAAATTGCTTTGAGCGGAGCTTACGCTTCGATTGGGTTATATGAAACGCCAAGTAAGG
AAACCAGGGAAAAAGCGATAGGTTTGTTAGAGGACTTGGGAGCAATTGAATATGCCGATC
GCCGCTATGAAACCCTTTCTCAAGGGGAAAAACAAAGAGCATTGATTGCTAGAGCACTAA
TGGCCGATCCGGAGCTGCTGATACTGGATGAACCAGTCACAGGACTGGATTTTATTGCCC
GGGAAAAGCTGTTAGATACGATTACATACATTGCAAACAAAGAAAATGCACCATCTATCC
TTTATGTGACTCATCATGCTGAAGAAATTTTGCCTGTCTTTGATAAAGCCCTTTTATTAA
AACAGGGAGAGGTTTTTGGATCCGGAGAAATAAAGGAAATGCTTACTGATCAAATACTTT
CCGCTTTTTTTGATACGCCAATCCATGTATTATGGAATCAGGATCGGCCGTTTTTAACAA
GAGCTGAGCCGATAACGAATGCCTGACAAATATATATAGATTCATCCTAGGGGTGCTTTG
                                       <----------------F
CGAAGCTGAGAGAGACTTTGTCTCAACCCTTTTGACCTGATCTGGATCATGCCAGCGGAG
GGAAGCGGTGAAAAGCGGAGTACATCGGACTCC
     ↑                 <-SQ7-R
```

Fig. 3

SEQUENCE LISTING

<160> NUMBER OF SEQ ID NOS: 16

<210> SEQ ID NO 1
<211> LENGTH: 28
<212> TYPE: DNA
<213> ORGANISM: Artificial
<220> FEATURE:
<223> OTHER INFORMATION: Oligonucleotide primer

<400> SEQUENCE: 1
ccggaattcg ctgtcggcag atggagag                                28

<210> SEQ ID NO 2
<211> LENGTH: 38
<212> TYPE: DNA
<213> ORGANISM: Artificial
<220> FEATURE:
<223> OTHER INFORMATION: Oligonucleotide primer

<400> SEQUENCE: 2
gtatccaccc cgcagatttc gactttattt ctcgacac                     38

<210> SEQ ID NO 3
<211> LENGTH: 38
<212> TYPE: DNA
<213> ORGANISM: Artificial
<220> FEATURE:
<223> OTHER INFORMATION: Oligonucleotide primer

<400> SEQUENCE: 3
gaaatctgcg gggtggatac ccggcaatag ttaccctt                     38

<210> SEQ ID NO 4
<211> LENGTH: 38
<212> TYPE: DNA
<213> ORGANISM: Artificial
<220> FEATURE:
<223> OTHER INFORMATION: Oligonucleotide primer

<400> SEQUENCE: 4
gtatccaccc cgcagatttc ccttcttcaa ctaacggg                     38

<210> SEQ ID NO 5
<211> LENGTH: 38
<212> TYPE: DNA
<213> ORGANISM: Artificial
<220> FEATURE:
<223> OTHER INFORMATION: Oligonucleotide primer

<400> SEQUENCE: 5
gaaatctgcg gggtggatac ctcaagcgca ggtgtcca                     38

<210> SEQ ID NO 6
<211> LENGTH: 28
<212> TYPE: DNA
<213> ORGANISM: Artificial
<220> FEATURE:
<223> OTHER INFORMATION: Oligonucleotide primer

<400> SEQUENCE: 6
ccggaattcg cacccctagg atgaatct                                28

<210> SEQ ID NO 7
<211> LENGTH: 32

```
<212> TYPE: DNA
<213> ORGANISM: Artificial
<220> FEATURE:
<223> OTHER INFORMATION: Oligonucleotide primer

<400> SEQUENCE: 7
gcgcaagctt ccaagacgga gatgaaagat ga                                32

<210> SEQ ID NO 8
<211> LENGTH: 33
<212> TYPE: DNA
<213> ORGANISM: Artificial
<220> FEATURE:
<223> OTHER INFORMATION: Oligonucleotide primer

<400> SEQUENCE: 8
gccgaagctt tatttgccgt tcatgtttaa ggc                               33

<210> SEQ ID NO 9
<211> LENGTH: 3248
<212> TYPE: DNA
<213> ORGANISM: Artificial
<220> FEATURE:
<223> OTHER INFORMATION: Deletion region on B. Subtilis RS303 comprising
      the cat sequence

<400> SEQUENCE: 9
cgattatgac aaaagaagaa atgatttctg cagataaatg tttaatcggt atcagcacaa    60
caaagctgtc ggcagatgga gagtttgacg cgattattca tccgaaaatg ctttcgggca   120
aggctgtcaa acacgtttca taatgttcgc aaatgtccgt tacttatcat actcaaacgg   180
cgtgacattt agaagggaga ggaagatgaa aaaactgaaa ttacggttga cgcacctctg   240
gtataagctg ctgatgaaac ttgggctgaa agtgatgaa gtctattaca taggcgggag    300
tgaagccctg ccgcctccat tatctaaaga tgaggagcag gttttgttaa tgaagctccc   360
aaacggcgat caggcggcgc gcgccattct aattgaacgc aatttgcgtc tggtcgtata   420
tatcgcccgt aaatttgaaa atacgggaat taatatagag gatttaatca gcatcggtac   480
catcggtcta atcaaagctg ttaatacatt taatccagaa aagaaaatca gcttgctac    540 ctatgcctcc cggtgtatag aaaatgaaat cctgatgtat ttaagaagaa ataacaaaat   600
ccgttcagag gtttcctttg atgaaccgct taatattgat tgggacggca atgagctttt   660
gctttctgat gtgctcggca ctgacgatga catcatcact aaagacatag aagctaacgt   720
cgataaaaag cttttgaaaa aagcgcttga acagcttaat gagagagaaa agcaaatcat   780
ggagctgcgg tttgggcttg tcggtgaaga agaaaaaacc caaaggatg tagcggatat    840 gatgggggatt tctcagtctt atatttcgcg gcttgagaaa agaattataa aaaggttgag   900
aaaagagttc aacaaaatgg tgtaaaaaat tttatggtta gaaccccttg attttacagg   960
gatttcctga tttcgacagt ttttcggtct gagtgcagtg catattttc ccacccaagg    1020 agatacttaa cgttgtacag cagctcctgt agggagggaa aaagtgtcg agaaataaag    1080 tcgaaatctg cggggtggat acccggcaat agttaccctt attatcaaga taagaaagaa   1140
aaggattttt cgctacgctc aaatccttta aaaaacaca aagaccaca ttttttaatg     1200 tggtcttta ttcttcaact aaagcaccca ttagttcaac aaacgaaaat tggataaagt    1260
gggatatttt taaaatatat atttatgtta cagtaatatt gactttttaaa aaggattga   1320 ttctaatgaa gaaagcagac aagtaagcct cctaaaattca ctttagataa aaatttagga   1380
ggcatatcaa atgaacttta ataaaattga tttagacaat tggaagagaa aagagatatt    1440
```

-continued

```
taatcattat ttgaaccaac aaacgacttt tagtataacc acagaaattg atattagtgt      1500
tttataccga aacataaaac aagaaggata taaattttac cctgcattta ttttcttagt      1560
gacaagggtg ataaactcaa atacagcttt tagaactggt tacaatagcg acggagagtt      1620
aggttattgg gataagttag agccacttta tacaattttt gatggtgtat ctaaaacatt      1680
ctctggtatt tggactcctg taaagaatga cttcaaagag ttttatgatt tatacctttc      1740
tgatgtagag aaatataatg gttcggggaa attgtttccc aaaacaccta tacctgaaaa      1800
tgctttttct ctttctatta ttccatggac ttcatttact gggtttaact taaatatcaa      1860
taataatagt aattaccttc tacccattat tacagcagga aaattcatta ataaaggtaa      1920
ttcaatatat ttaccgctat ctttacaggt acatcattct gtttgtgatg gttatcatgc      1980
aggattgttt atgaactcta ttcaggagtt gtcagatagg cctaatgact ggctttata       2040 atatgagata atgccgactg tacttttac agtcggcttt ctaatgtcac taacctgccc       2100
cgttagttga agaagggaaa tctgcggggt ggatacctca agcgcaggtg tccagacttg      2160
aaaaagcggc tatcaaacaa atgaataaaa atattcatca ataatgaaaa gcctttaaaa      2220
cgatgttgtt ttaaaggctt ttctattgat tatggatggt ttacgttttg gaaaaagtaa      2280
ggtatcctag ttcgtacaaa gttttatgaa aattaaaaca attataaaag gcaataaaga      2340
ggaggaccac gatgattttg cagcttgaca atgtctcact aaaacggaat gggaaatgga      2400
tactgaaaga tattcattgg aaggtggaag aaaaggaaaa ttgggtgctt tacggcctaa      2460
atggcgccgg gaagacagcg ctgttaaata tgctttgctc atattatttt ccaacatcag      2520
gcgagatgca ggtgctcggc catgaatttg gcaaaacaga gcttggggaa aagctcagac      2580
gtaaaattgg cctcgtctca gcagctcttc agcaaaaatt gtatccggca gattcagctt      2640
ttgaaattgc tttgagcgga gcttacgctt cgattgggtt atatgaaacg ccaagtaagg      2700
aaaccaggga aaaagcgata ggtttgttag aggacttggg agcaattgaa tatgccgatc      2760
gccgctatga aacccttcct caaggggaaa aacaaagagc attgattgct agagcactaa      2820
tggccgatcc ggagctgctg atactggatg aaccagtcac aggactggat tttattgccc      2880
gggaaaagct gttagatacg attacataca ttgcaaacaa agaaatgca ccatctatcc       2940 tttatgtgac tcatcatgct gaagaaattt gcctgtcttt gataaagcc cttttattaa       3000 aacagggaga ggttttttgga tccggagaaa taaaggaaat gcttactgat caaatacttt      3060
ccgctttttt tgatacgcca atccatgtat tatggaatca ggatcggccg tttttaacaa      3120
gagctgagcc gataacgaat gcctgacaaa tatatataga ttcatcctag gggtgctttg      3180
cgaagctgag agagactttg tctcaaccct tttgacctga tctggatcat gccagcggag      3240
ggaagcgg                                                              3248
```

<210> SEQ ID NO 10
<211> LENGTH: 20
<212> TYPE: DNA
<213> ORGANISM: Artificial
<220> FEATURE:
<223> OTHER INFORMATION: Oligonucleotide primer

<400> SEQUENCE: 10
tgcgttaaac cggatcacgt                                                    20

<210> SEQ ID NO 11
<211> LENGTH: 19
<212> TYPE: DNA

```
<213> ORGANISM: Artificial
<220> FEATURE:
<223> OTHER INFORMATION: Oligonucleotide primer

<400> SEQUENCE: 11
tgcactgcac tcagaccga                                                  19

<210> SEQ ID NO 12
<211> LENGTH: 19
<212> TYPE: DNA
<213> ORGANISM: Artificial
<220> FEATURE:
<223> OTHER INFORMATION: Oligonucleotide primer

<400> SEQUENCE: 12
gtagcggata tgatgggga                                                  19

<210> SEQ ID NO 13
<211> LENGTH: 21
<212> TYPE: DNA
<213> ORGANISM: Artificial
<220> FEATURE:
<223> OTHER INFORMATION: Oligonucleotide primer

<400> SEQUENCE: 13
cctgctgtaa taatgggtag a                                               21

<210> SEQ ID NO 14
<211> LENGTH: 20
<212> TYPE: DNA
<213> ORGANISM: Artificial
<220> FEATURE:
<223> OTHER INFORMATION: Oligonucleotide primer

<400> SEQUENCE: 14
catggacttc atttactggg                                                 20

<210> SEQ ID NO 15
<211> LENGTH: 21
<212> TYPE: DNA
<213> ORGANISM: Artificial
<220> FEATURE:
<223> OTHER INFORMATION: Oligonucleotide primer

<400> SEQUENCE: 15
ggtatcctag ttcgtacaaa g                                               21

<210> SEQ ID NO 16
<211> LENGTH: 19
<212> TYPE: DNA
<213> ORGANISM: Artificial
<220> FEATURE:
<223> OTHER INFORMATION: Oligonucleotide primer

<400> SEQUENCE: 16
ggagtccgat gtactccgc                                                  19
```

NON-SPORULATING *BACILLUS SUBTILIS* HAVING PARTS OF THE GENE ENCODING SIGMA G DELETED

FIELD OF THE INVENTION

The invention relates to a non-sporulating *Bacillus subtilis* strain, to a method for its preparation and to its use as a production organism. In addition, the invention relates to a method for the preparation of a biologically prepared product by using a non-sporulating bacterium.

BACKGROUND OF THE INVENTION

The bacteria of the *Bacillus* genus are used extensively in the production of different industrially significant enzymes. The most significant production hosts are *B. amyloliquefaciens* and *B. licheniformis* that are used as producers of proteases and amylases, for instance. Industrial processes generate significant amounts of bacterial mass that needs to be inactivated prior to its discharge into the environment, especially if the bacterium is a genetically engineered bacterium. Destroying sporulated production cells requires more intensive processing than asporogenous cells. The spores of *Bacillus* endure heat much better than vegetative cells and therefore, destroying them by heating requires high temperatures and long-term treatments. These treatments invariably increase the equipment and operating costs in the production. This is why it is desirable to use a non-sporulating *Bacillus* strain. The present invention provides a solution to the sporulation problem that significantly improves the use of *B. subtilis* as a production organism.

Sporulation is a multistage (I to VII) event that is initiated in certain growth conditions in which first a pre-spore is created inside the mother cell. Finally, the mother cell dies and the mature spore is freed. The spore can endure a higher degree of dehydration and heat than the mother cell and thus ensures the survival of the bacterium in unfavourable conditions. In favorable conditions, the spore is activated and the division of the bacterial cell is restarted. The different stages of sporulation have been established by research on gene mutations affecting sporulation. Over 125 genes affecting sporulation are known (Stragier and Losick, 1996).

The production of proteins using a *Bacillus* bacterium incapable of sporulation is disclosed in WO97/03185, for instance, which proposes the elimination of sporulation by mutating the sporulation genes. The publication describes the deletion of the sporulation gene spoIIAC from *Bacillus licheniformis*. The deletion was performed using a temperature-sensitive plasmid to which a PCR product prepared by the SOE (splicing by overlap extension) technique was introduced, in which product the regions on both sides of the spoIIAC gene were joined together in such a manner that the spoIIAC gene in the middle was removed. The SOE technique is described in U.S. Pat. No. 5,023,171, for instance. The in vitro deletion mutation can be introduced inside the bacterial cell by means of the plasmid, and the replication of the free plasmid can be prevented by raising the temperature, thus revealing the recombinant bacteria in which the plasmid is inserted in the chromosome. The deletion of the desired gene takes place when the plasmid detaches from the chromosome in a certain manner. In said WO patent publication, the described technique was, however, unable to delete the spoIIAC gene from the *B. subtilis* bacterium. The recombination at the detaching stage of the plasmid always occurred in such a manner that the spoIIAC gene remained intact.

Non-sporulating *B. subtilis* strains are, however, described elsewhere. EP 164,117 relates to a *B. subtilis* strain with a mutation in the spoIIA gene, EP 492,274 relates to a *B. subtilis* strain with a mutation in the spoIID gene, and U.S. Pat. No. 4,450,235 and U.S. Pat. No. 4,450,236 relate to a *B. subtilis* strain with a deletion in the spoOA gene. Said genes are associated with sporulating stage II or an earlier stage.

One of the known genes of the next sporulating stage (III) is the sigG gene (=spoIIIG gene) that codes the sigma-G factor which binds to an RNA polymerase that in turn can bind to the promoter of certain sporulating genes in the pre-spore. This sigma-G factor is necessary at the third stage of sporulation, and it is known to control at least 19 gene transcriptions (Ishii et al., 2001). The products of the genes associated with the Sigma-G control system improve the survival ability and re-germination of the spores (Haldenwang, 1995).

Fougler and Errington (1989) have described a *B. subtilis* 646 strain that is a spontaneously formed sigG mutant. The only thing known of the mutation is that it is outside the promoter and 30 first codons. This information has been obtained from an active spoIIIG-lacZ fusion that was inserted into the chromosome. In the case of such spontaneous or induced random mutants, the location or exact action of the mutation is usually not known. The reverse-mutation possibility, i.e. the reversal of sporulation as it was, of such strains cannot be controlled and the possibility of various suppressor mutations is also high. Since the location of the mutation is not known, it is usually not possible, either, to know whether a changed protein is created. In addition, a mutation in another gene can, for instance, suppress the effect of the original mutation. Attempts have also been made to inactivate the sigG gene by making insertions, for instance. Illing et al. (1990), for instance, cloned a HindIII-Pst1 fragment of 320 base pairs from sigG to an integration plasmid and obtained as a result of the integration a non-sporulating *B. subtilis* strain N15 (trpC2 spoIIIG::pSGMU422). The integration plasmid, however, detached from the chromosome without selection pressure with chloramphenicol, and consequently, this type of strain is not suitable as a production host.

Karmazyn-Campelli et al. (1989) have described the inactivation of the sigG gene by inserting a 1.5-kb chloramphenicol resistance cassette (cat) between codons 166 and 167 (spoIIIG::cat). This insertion was, however, done in such a manner that the sigG gene still remained, even though cut, in the chromosome. Thus, there is a risk of reverse-mutation. Even though a strain inactivated by cat insertion cannot recombine, the deletion may return the activity of the sigG gene and the sporulation of the strain back to normal.

Karmazyn-Campelli et al. (1989) have further deleted a fragment of the sigG gene, 70 base pairs, between codons 18 and 42. The effect of this deletion (spoIIIGΔ1) on sporulation remains, however, unclear, because during the deletion, an extra HaeIII fragment of 18 base pairs unexpectedly appeared between said codons from pUC8 used as the cloning vector. This extra fragment had a stop codon right at the beginning, so there is no certainty that the deletion of 70 base pairs is sufficient for ending sporulation. Without the extra fragment, at least a partly functioning sigma factor could be created even after the deletion, especially since the deletion does not include regions which are believed to be significant in binding to target promoters. In other words, it did not become clear, whether the inactivation of the sigG gene was caused by the deletion or merely by the extra stop codon.

Kim J.-H. et al. 2001 have described a *B. subtilis* mutant with a deletion in the spoIIIG gene. The deletion in question was only one nucleotide long and resided outside the functional regions of the gene (sigG gene nucleotide 397, tymidine (T) deleted). A kanamycin-resistance block (kana') was inserted after the deletion site. This produced mutants with a reduced sporulation capability. There is no information on the stability of the strain. The reversion frequency of one nucleotide is, however, significant, and this kind of strain is, therefore, not recommended as the production host of a foreign protein.

Studies published earlier have usually examined the different stages of sporulation and related mutants, without focusing on their stability. Consequently, none of the above sigG mutants of the *B. subtilis* bacterium are suitable as a production strain, of which a permanent, i.e. non-reversible, sporulation mutation is required. The present invention now provides a fully non-sporulating, stable *B. subtilis* strain suitable as a production strain. In addition, the sporulation gene is deleted in such a manner that it has no unfavourable effects on the production of the desired product or its properties.

SUMMARY OF THE INVENTION

The invention relates to a non-sporulating *B. subtilis* strain characterized in that at least 150 nucleotides are deleted from its sigG gene. The deletion presented herein is the first with which it is possible to show beyond dispute the effect of the sigG deletion in preventing sporulation. Moreover, in gene deletion, it is difficult to predict, how the deletion affects the other functions of the organism or its ability to survive as a whole. The present invention does, however, show that the deletion of the sigG gene did not affect the other essential functions of the mutated bacterium, such as its ability to produce recombinant polypeptide.

The present invention also provides a method for the preparation of a non-sporulating *B. subtilis* strain, characterized in that at least 150 nucleotides are deleted from the sigG gene of the *B. subtilis* strain. Further, the invention relates to the use of the presented non-sporulating *B. subtilis* strain as a production organism. The invention further includes a method for the preparation of a biologically prepared product, the method being characterized in that the product is prepared using the non-sporulating *B. subtilis* strain of the invention.

Preferred embodiments of the invention are described in the dependent claims.

BRIEF DESCRIPTION OF THE FIGURES

FIG. 2 shows the nucleotide sequence of the deletion region of the non-sporulting *B. subtilis* strain RS303 (SEQ ID NO: 9).

DETAILED DESCRIPTION OF THE INVENTION

The *B. subtilis* of the invention is made non-sporulating by deleting a significant fragment of the sigG gene, which in this context means at least approximately 150 and preferably at least approximately 300 nucleotides. The sigG gene has at least two functional regions, i.e. regions significant for the activity of the protein, of which one codes a domain that presumably binds itself to the core fragment of the RNA polymerase and begins from amino acid no. 67 and ends at amino acid no. 80. This domain is defined by comparing the amino acid sequence of the sigma-G factor of the *B. subtilis* bacterium with other known sigma factor sequences. Another important functional region is the H-T-H (helix-turn-helix) motif that is present in proteins binding themselves to the DNA, also defined on the basis of similarity and covers the amino acids 229 to 248 of the SigG protein. The region to be deleted preferably resides in the region between the nucleotides coding the amino acids no. 67 and 248 of the SigG protein. More preferably, the deletion comprises at least a part of one of the two functional regions of the sigG gene, which regions code for amino acids 67 to 80 or correspondingly 229 to 248 of the sigG protein, and in particular, the deletion comprises at least a part of both of said functional regions of the sigG gene. Alternatively, the deletion can also reside between the functional regions so that the expression of either of the functional regions is prevented and/or the distance between them changes in the native sigma-G factor-like molecule in such a manner that the binding of the sigma-G factor to the RNA polymerase and DNA is prevented. According to one embodiment, at least 600 and especially at least 670 nucleotides are deleted from the sigG gene. It is expedient to delete nucleotides 39 to 715, for instance. It is also possible to delete the entire sigG gene and the promoter region of the gene.

The sigG gene can be deleted in many different ways. Preferably, an insert is first prepared by the SOE (gene splicing by overlap extension) technique, which means that the nucleotide fragments required for the insert are first amplified by a PCR reaction, the primers of which are designed in such a manner that the fragments amplified in the PCR reaction can be ligated through a second PCR reaction by using a complementary sequence, i.e. overlap region. An expedient insert contains the flanking regions of the gene being deleted and at least one selection marker gene. The flanking region refers herein to adjacent regions up- and downstream from the gene region to be deleted that are not deleted. The selection marker gene is a gene that codes for any selectable property, such as enzyme, that relates to the formation of a specific metabolite or antibiotic resistance.

The insert being prepared can be either a plasmid or preferably a linear DNA, in which case the selection marker gene resides between the flanking regions. *B. subtilis* is then transformed with this insert, i.e. "exchange cassette," the ends of which are homologous with the flanking regions of the gene being deleted. As a result of two simultaneous crossing-overs between homologous regions, the insert integrates to the chromosome of the bacterium in place of the deleted sigG gene. A deletion performed using such a homologous double recombination is described in U.S. Pat. No. 4,963,487, for instance. The selection marker gene thus replaces the deleted sigG gene region. The desired transformants, from which the sigG gene is deleted, can then be screened by subjecting the bacteria to the selection pressure determined by the selection marker gene. The non-sporulating bacteria of the invention are stable and cannot regain their sporulation ability even if the inserted selection marker gene was deleted from the chromosome.

The sigG gene deletion described above is presented in FIG. 1 that will now be explained in detail. Three DNA products AB, CD and EF are prepared by a PCR reaction by using primers A and B, C and D, and E and F, respectively.

Products AB and EF are prepared from the chromosomal DNA of the *B. subtilis* bacterium and product CD from a suitable plasmid, for instance. AB comprises the flanking region (end of spoIIGA and sigE) upstream from the sigG gene and EF comprises the flanking region (beginning of ylmA) downstream from the sigG gene. Product CD comprises the selection marker gene that in this case is a chloramphenicol resistance gene (cat) obtainable for instance from plasmid pHV14 (Ehrlich, 1978) or pC194 (Horinouchi and Weisblum, 1982). The primers used in PCR are such that the obtained PCR products AB, CD and EF can be ligated by means of partly overlapping complementary sequences. Primers B and C and primers D and E, respectively, are thus partly complementary. Three PCR products can be ligated in two steps. According to FIG. 1, first AB+CD and CD+EF are ligated, after which the obtained PCR products AD and CF are ligated utilizing the homologous regions having the length of product CD to obtain the desired insert AF, which thus contains (in order 5'→3') the sigG gene flanking region (sigE, for instance), the chloramphenicol resistance gene (cat) and the second flanking region (beginning of ylmA) of the sigG gene. A corresponding insert can alternatively be constructed by first preparing AD, for instance, and ligating it with product EF, or by first preparing CF and ligating it with product AB. The *B. subtilis* bacteria are then transformed with the obtained insert AF and the desired transformants are screened in the presence of chloramphenicol.

Figure 1:
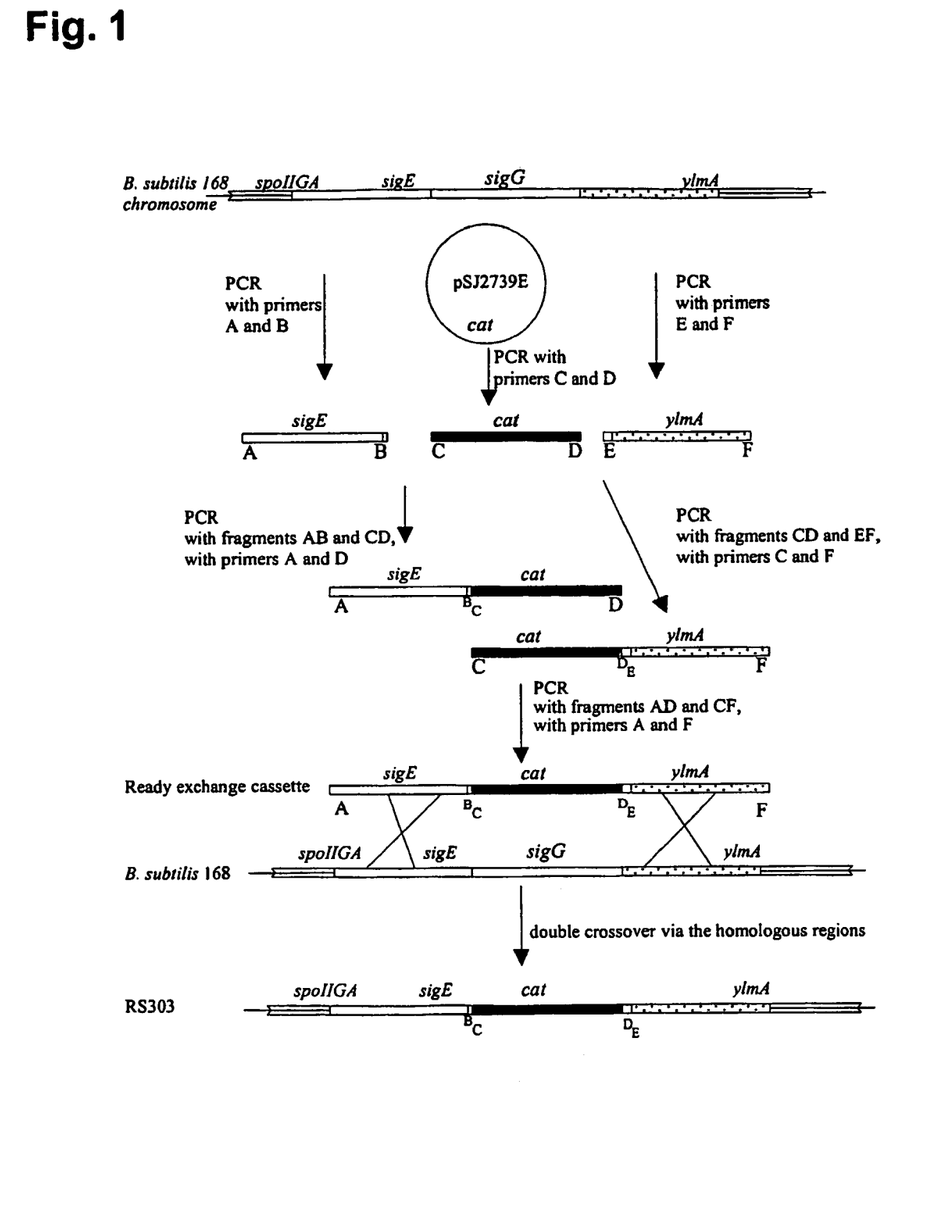
FIG. 1 is a schematic view of the deletion of the sigG gene.

The primers described above can also be designed so that the overlap region upstream from the selection marker gene is homologous with the overlap region downstream from the selection marker gene. This permits the deletion of the inserted cat gene later from the deletion region. The deletion of the cat gene can take place in such a manner that products AB and EF are ligated through a PCR reaction by using the overlap region to produce product ABEF that is then used to transform the above SigG$^-$, Cat$^+$ transformant to delete the cat gene from the transformant. Said homologous overlap regions also permit the deletion of the cat gene with homologous recombination by means of a repeating overlap region in the sequence.

In designing the primers used in the SOE technique, general rules are followed, of which Sambrook and Russell (2001), for instance, have made a summary. It should especially be noted that to join together DNA fragments, the overlap regions should be at least 20 to 25 nucleotides long to permit the use of sufficiently high annealing temperatures in PCR to ensure specificity (McPherson and Møller, 2000). Shorter overlap regions of approximately 15 nucleotides can be used if a less complex DNA, such as a plasmid, is used as the template instead of a chromosomal DNA. When using synthetic primers, their maximum length could be approximately 100 nucleotides according to the present technique. DNA fragments that have been denatured to be single stranded and made with PCR or spliced with restriction enzymes or mechanically from a macromolecular DNA can also be used as primers, in which case the maximum length of the primers cannot be defined exactly, but can even be several tens of thousands of nucleotides. The success of the joining of the DNA fragments used in deletion also depends on the purity of the PCR products. When a gene or a part of it is to be deleted, it is important that the PCR reaction of the final SOE product no longer has the template used in the beginning, in which the complete gene is intact.

In *B. subtilis*, the recombination between the chromosome and the homologous DNA region in the plasmid is efficient. It has been suggested that 150 base pairs of homologous DNA in a plasmid that does not replicate in *B. subtilis* is enough for integration (Ferrari and Hoch, 1989). Khasanov et al. (1992) used a plasmid with a heat-sensitive replicon and showed that 70 nucleotides were enough for an integration occurring using homologous recombination. The above-mentioned plasmids integrated with the chromosome through one crossing-over contrary to a linear DNA, the integration of which requires that the homologous recombination occur simultaneously at two sites. When transforming with DNA produced by a linear SOE technique, the homologous regions should be longer than 70 to 150 nucleotides so that it is possible to detect the integration of the SOE fragment to the chromosome with the prior art transformation methods. A region homologous with the regions flanking the gene to be deleted of the linear DNA insert comprises at least several hundreds of base pairs or even at least a thousand base pairs.

The maximum length of the homologous region is mainly determined on the basis of the properties of the DNA polymerase used in PCR. The present PCR enzymes are capable of amplifying DNA fragments of several tens of kilobase pairs, but at the same time the probability of mutations in the created DNA fragments increases. A practical maximum length of the homologous region is, however, presumably approximately 5 kilobases (kb). It is recommended especially that the flanking region upstream from the deleted region of the DNA insert, the selection marker gene and the flanking region downstream from the deleted region all have substantially the same length. Most preferably, the length of the homologous region is approximately 1 kb and the length of the entire linear insert is approximately 3 kb.

The deletion of the gene can also be done using a two-stage homologous recombination. The method is described with *Lactococcus lactis* (Biswas et al., 1993), and the spoIIAC gene of *B. licheniformis* is deleted with the same method (WO97/03185). Both cases utilize a plasmid, the replication of which is heat sensitive and which has an antibiotic resistance marker. The flanking regions of the region to be deleted are first inserted sequentially and in the same direction into a plasmid, such as pE194, suitable for the *B. subtilis* bacterium. The plasmid is transformed to the competent bacterium at a temperature of 32° C. allowing replication, and the obtained transformants are grown at 45° C., whereby only the bacteria in which integration to a chromosome has taken place can grow on a chloramphenicol medium. As a result of the integration, two pairs of homologous regions are formed in the chromosome, between which a second recombination may take place when the transformants are grown without chloramphenicol at 32° C. A recombination between one of the homologous pairs leads to both the detaching of the plasmid and the deletion of the region between the homologous regions in the plasmid in the chromosome. The length of the used homologous regions can be 70 to 2,500 base pairs. In the described manner, it is possible to perform several successive deletions from the same strain, because nothing extra, such as an antibiotic selection marker, remains in the chromosome.

Further, the desired deletion can be performed using the two homologous regions in the plasmid. The deletion structure, which comprises the flanking regions on both sides of the deletion and the selection marker between them, can then be inserted into a plasmid that does not replicate in the *B. subtilis* bacterium (e.g. pJH101) or whose replication depends on the temperature (pE194). The obtained plasmid is transformed to the competent bacterium and resistant transformants are screened. These methods usually require the use of two selection markers to distinguish the transformants in which recombination has taken place through just one homologous region and not both of them.

mase pen P of *Bacillus licheniformis*. In said plasmid, pen P is inserted at the HindIII cloning sites of secretion vector pKTH141 (Lundström, 1985). The α-amylase promoter of the vector and the fragment coding the signal sequence is derived from the *Bacillus amyloliquefaciens* bacterium.

TABLE 1

Bacterial strains and plasmids

| STRAIN | DELETION REGION | PROPERTIES | SELECTION MARKER | PLASMID | SELECTION |
|---|---|---|---|---|---|
| 168 | | *B. subtilis* 168 wild strain[a] | | | |
| RS303 | SigG | Non-sporulating | cat | | Cm |
| RS310 | SigG | Non-sporulating | cat | pRSH10 | Cm, Km |
| RS201 | | *B. subtilis* 168 wild strain[a] | | pRSH10 | Km |

[a]Ref. Kunst, F. et al., 1997

The non-sporulating *B. subtilis* bacterium, from which the sigG gene has been substantially deleted, is suitable for a production strain of various biologically prepared products. A biologically prepared product refers to a compound that an organism can produce. Usually, it is a biologically active compound. Preferably, this product is extracellularily secreted by the cell. The product can be either a natural product of a bacterium or a product formed as a result of genetic engineering. Genetic engineering can also be used to engineer metabolism routes or introduce new enzymes into a bacterium to accumulate such quantities of existing or completely new metabolites that their isolation is worthwhile.

The prepared products can be polypeptides, for instance, that are intended for medical use, such as bacterium-based β-lactamases, mammary transmitter substances, such as peptide hormones and interferons. A non-sporulating bacterium is also suitable as the production host of industrially significant enzymes, such as proteases, amylases, pullulanases, xylanases, pectinases, β-lactamases, xylose isomerases and betaglucanases. In addition, it is possible to produce sugars, nucleosides, acids, vitamins, amino acids and surfactants, i.e. lipopeptides or rhamnose lipids that lower surface tension.

According to one embodiment, DNA that codes a desired polypeptide, such as β-lactamase, is inserted into the non-sporulating *B. subtilis* strain, the DNA is expressed in the cell and the obtained recombinant polypeptide is recovered from the cell or the growth medium. The introduction of the DNA required for the expression of the desired polypeptide or metabolite can be performed with a technique that is for instance transformation using natural competence or electroporation, or with any technique suitable for the *B. subtilis* bacterium.

EXAMPLE

Bacterial Strains and Plasmids

The properties of the bacterial strains and plasmids used in the example are listed in Table 1. The sequence of the *B. subtilis* 168 sigG gene of the host organism and its flanking regions was obtained from a data bank. The region coding the cat gene originates from plasmid pSJ2739E and is the same as that of the plasmid pC194 of the *Staphylococcus aureus* bacterium (GenBank accession no. V01277). Production vector pRSH10 is a plasmid that codes the β-lacta- Growth Conditions The bacterial strains were grown on a Luria Broth (LB) medium (Harwood and Cutting, 1991), 5 g/l yeast extract (Difco), 10 g/l trypton (Oxoid) and 10 g/l NaCl (Merck), in an agitation growth, +37° C., 250 rpm. When monitoring the protein production, the cells were grown on a concentrated LB medium (10 g/l yeast extract, 20 g/l trypton and 10 g/l NaCl). Chloramphenicol (Cm) 5 µg/ml and kanamycin (Km) 10 µg/ml were used for selection in the bacterial growth.

DNA Techniques

DNA techniques were used with conventional methods (Sambrook et al., 1989). The chromosomal DNA was isolated according to Marmur's (1961) instructions. The plasmid DNA was isolated from the bacterial cells in an ion exchange column (QIAGEN Plasmid Midi Kit) according to the manufacturer's instructions (Qiagen Plasmid Purification Handbook July/1999). Departing from the instructions, a lysozyme treatment was added to the protocol to degrade the peptidoglucane layer, and in the treatment 1 mg/ml lysozyme was added to buffer P1 and the cells were incubated in the buffer at +37° C. for 30 minutes. The purified plasmid was dissolved in 30 to 100 µl of sterilized water. The DNA content of the plasmid preparates was 50 to 500 ng/µl.

Sporulation Tests

The effect of sigG deletion on sporulation was tested by growing bacterial cells in a sporulation medium and by thermally treating (+85° C., 10 min) the cells (Harwood and Cutting, 1991). The used treatment kills vegetative cells, but is not enough to kill the spores. The number of colonies grown after the treatment indicates the amount of spores.

The bacterial cells of the logarithmic stage were inoculated 1:100 to a sporulation medium (Schaeffer's sporulation medium, SS: 8 g nutrient broth, 1 g KCl, 0.12 g $MgSO_4 \times 7H_2O$, 0.5 ml 1M NaOH, 1 ml $Ca(NO_3)_2 \times 4H_2O$, 1 ml 0.01M $MnCl_2 \times 4H_2O$, 1 ml 0.0001 M $FeSO_4 \times 7H_2O$) and grown for 24 hours (+37° C., 250 rpm). To calculate the cell density in the bacterial growth, serial dilutions ($10^{-1}$ to $10^{-9}$) were made in a dilution buffer (5 ml 0.1 M K-phosphate buffer, pH 7.4, 2.5 ml 1M KCl solution, 5 ml 10 mM $MgSO_4$ solution, 37.5 ml sterilized water), and the dilutions $10^{-5}$ to $10^{-9}$ were plated onto LB plates (100 µl/plate). The plates were incubated overnight at +37° C. in a temperature cabinet, the number of colonies were calculated and given per milliliter.

To determine the amount of spores, the cells were thermally treated. The cells were heated for 10 minutes at +85°

C. in a temperature-controlled bath. After the thermal treatment, the cells were plated onto LB plates. The plates were incubated for 17 hours at +37° C. The number of colonies grown on the plates was calculated (per ml). In the sporulation tests, wild strain 168 was used as the control strain and treated in the same manner as the tested strains.

Preparing sigG Gene Deletion

The sigG gene deletion was performed by transforming the wild strain B. subtilis 168 with a linear recombinant DNA fragment constructed using PCR and the SOE technique (Horton et al., 1989, and U.S. Pat. No. 5,023,171). A flowchart of the performed deletion is shown in FIG. 1. The primers of the PCR reactions were designed in such a manner that the PCR products could be joined by a second PCR reaction using a complementary sequence. Table 2 lists the primers used in the PCR reactions. In the table, the mutually complementary regions in the primers are marked in bold and underlined. The complementary region used in the primers is an region of 20 nucleotides that begins from nucleotide 19 of the sigG gene. Primer B codes this region from the starting codon of the sigG gene. Primers B and D and C and E, respectively, are partly homologous.

TABLE 2

Primers used in SOE reactions

| | | |
|---|---|---|
| A | 5'CCGGAATTCGCTGTCGGCAGATGGAGAG3' | (SEQ. ID NO.: 1) |
| B | 5'GTATCCACCCCGCAGATTTCGACTTTATTTCTCGACAC3' | (SEQ. ID NO.: 2) |
| C | 5'GAAATCTGCGGGGTGGATACCCGGCAATAGTTACCCTT3' | (SEQ. ID NO.: 3) |
| D | 5'GTATCCACCCCGCAGATTTCCCTTCTTCAACTAACGGG3' | (SEQ. ID NO.: 4) |
| E | 5'GAAATCTGCGGGGTGGATACCTCAAGCGCAGGTGTCCA3' | (SEQ. ID NO.: 5) |
| F | 5'CCGGAATTCGCACCCCTAGGATGAATCT3' | (SEQ. ID NO.: 6) |

In the PCR reaction mixture (100 µl), 20 to 50 ng of DNA was used as the template, 30 pmol of each primer, 0.2 mM of dNTP (Boehringer Mannheim GmbH, Germany), 0.5 µl of Expand enzyme (Boehringer Mannheim GmbH, Germany) and 10 µl of 10xExpand buffer. 50 µl of mineral oil was pipetted on the reaction mixture and the reactions were made using PTC-100 Programmable Thermal Controller (MJ Research, Inc.). The PCR reactions were made with the following basic program consisting of a denaturising step (94° C., 4 min) and two subsequent cycles (94° C., 1 min; 50° C., 45 s; 72° C., 4 min) and 25 cycles (49° C., 1 min; 70° C., 45 s; 72° C., 4 min), followed by a 10-minute incubation at 72° C. The annealin temperatures of the primers were optimised to suit each reaction. The end products of the PCR reactions were purified from the reaction mixture (Qiagen Giaquick PCR purification kit, Qiagen GmbH, Germany) according to the manufacturer's instructions (QIAquick Spin Handbook/April 2000) and eluted into water (50 µl). The final DNA concentration of the purified product was 30 to 50 ng/µl. The end products of the PCR reaction were analysed with 1% agarose gel electrophoresis.

In preparing the sigG gene deletion, the first step was to prepare PCR products AB (1047 nucleotides, nt) and EF (1069 nt) coding the flanking regions of sigG with primers A and B and E and F, respectively. 20 ng of purified chromosomal DNA of the wild strain 168 was used as a template in the PCR reactions. The 1054-nucleotides long region CD coding the cat gene was amplified using primers C and D. 50 ng of purified plasmid pSJ2739E to which the cat gene was inserted from pHV14 was used as a template in the PCR reaction. The PCR product amplified from pSJ2793E used in this invention contains the same region of the cat gene and its surroundings as described in sequence V01277 (GenBank), starting from nucleotide 973 and ending in nucleotide 1985. Products AB and CD were amplified with the basic program. In the case of reaction EF, the annealing temperature of the basic program was lowered to 45° C.

In the next steps, 2.1-kb long PCR products AD (2081 nt) and CF (2103 nt) were prepared with two different reactions. The PCR products purified from the reaction mixture served as a template in the SOE reactions. PCR products AB and CD were ligated using a 20-nt long complementary region. The reaction mixture contained approximately 30 ng of both end products and the PCR reaction was performed with primers A and D according to the basic program. In the second SOE reaction, CD and EF were ligated using a complementary region to product CF. In this reaction mixture, approximately 30 ng of both products CD and EF were used as templates and the concentration of primers C and F was 30 pmol each. In this reaction, 25 cycles of the basic program were performed in different conditions (94° C., 1 min; 76° C., 45 s; 72° C., 4 min).

Recombinant DNA AF (3130 nt) was prepared from end products AD and CF that were joined together utilizing the region coding the cat gene and having the same length as product CD. This 1-kilobase long region is complementary in products AD and CF. For the PCR reaction, a reaction mixture was prepared containing approximately 100 ng of end products AD and CF purified from the reaction mixture of the PCR reactions described above, and 30 pmol of primers A and F. Product AF was amplified with the basic program.

The deletion of the sigG gene was prepared by transforming the competent cells of the wild strain by using the linear recombinant DNA AF. The preparation of the competent cells (Gryzan et al., 1978) was started by suspending B. subtilis 168 cells from a plate in 600 µl of GMI medium (modified minimal medium: 0.5 ml 20% glucose, 0.1 ml 10% casamino acids, 0.12 ml 10% yeast extract, 2.0 ml 500-µg/ml trypton, 0.03 ml 1M MgCl$_2$, 17.25 ml SMS (Spizizen Minimal Salts)), which was used to inoculate 10 ml of GMI medium in such a manner that the optical density (Klett-Summerson photometer) was approximately 30. The cells were incubated in an agitation growth to an early stationary phase (37° C., 250 rpm). The growth was transferred to 100 ml of minimal medium GMII (modified minimal medium: 0.5 ml 20% glucose, 0.1 ml 10% casamino acids, 0.12 ml 10% yeast extract, 1.875 ml 200-mM Ca(NO$_3$)$_2$, 143.1 ml SMS) and grown in the same conditions for 90 minutes. The cells were centrifuged (7000×g, 5 min) and suspended in 7 ml of supernatant.

The competent cells of the wild strain B. subtilis were transformed using the linear PCR product AF. 10 µl (DNA>2 µg) of the product of the PCR reaction was used in the transformation. In the transformation, 10 µl of recombinant DNA AF and 0.05 µg/ml chloramphenicol for inducing the cat gene were added to 500 µl of transformation solution (Gryczan et al., 1978). The cells were incubated at +37° C., 30 min (180 rpm) and the cells were plated on LB plates comprising 5 µg/ml of chloramphenicol for the selection.

The transformation produced three transformation colonies. The non-sporulating sigG-deleted strain has been named RS303.

Checking SigG Gene Deletion Construction by Sequencing

The stability of the deletion region was ensured by sequencing the chromosomal DNA of the bacterium in the deletion region and its flanking regions. PCR products were prepared from the chromosomal DNA and sequenced. Freeze-dried primers (Amersham Pharmacia Biotech) were dissolved in 100 µl of water, and a 3-µM (3-pmo/µl) dilution was prepared from the primers for the PCR reactions. A 5-µM (5-pmol/µl) dilution was prepared from the primers for sequencing.

Ensuring Stability of Deletion Regions of Non-Sporulating Strains RS202 and RS310

The primers used for the PCR products required for sequencing the deletion region from the chromosomal DNA of the strains RS303 and RS310 are shown below. The location of the primers in the sequence is shown in FIG. 2.

```
                        (SEQ ID NO.: 10)
SQ1-F       5'TGCGTTAAACCGGATCACGT3'

(SEQ ID NO.: 11)
SQ2-R       5'TGCACTGCACTCAGACCGA3'

(SEQ ID NO.: 12)
SQ3-F       5'GTAGCGGATATGATGGGGA3'

(SEQ ID NO.: 13)
SQ4-R       5'CCTGCTGTAATAATGGGTAGA3'

(SEQ ID NO.: 14)
SQ5-F       5'CATGGACTTCATTTACTGGG3

(SEQ ID NO.: 15)
SQ6-F       5'GGTATCCTAGTTCGTACAAAG3'

(SEQ ID NO.: 16)
SQ7-R       5'GGAGTCCGATGTACTCCGC3'
```

The stability of the sigG deletion region of the non-sporulating strains RS303 and RS310 was ensured by sequencing three PCR products amplified using primers SQ1-F to SQ7-R: SRS12, SRS34 and SRS567. The following table shows the size of the PCR products and the primers used to sequence the PCR reactions.

| Sequenced product | Size (bp) | Primers | Sequenced with primer |
| --- | --- | --- | --- |
| SRS12 | 1024 | SQ1-F/SQ2-R | SQ1-F/SQ2-R |
| SRS34 | 1070 | SQ3-F/SQ4-R | SQ3-F/SQ4-R |
| SRS567 | 1450 | SQ5-F/SQ7-R | SQ5-F/SQ6-F/SQ7-R |

The PCR products were analysed with agarose gel electrophoresis (1% gel). Product SRS 12 was purified from the reaction mixture (Qiagen Giaquick PCR purification kit, Qiagen GmbH, Germany) according to the manufacturer's instructions (QIAquick Spin Handbook/April 2000) and eluded in water (50 µl). Products SRS34 and SRS567 were isolated from the agarose gel due to the impurities in the product. The purification from the gel was performed with a commercial column (Qiagen Gel Extraction kit) according to the manufacturer's instructions (QIAquick Spin Handbook/April 2000) and the products were eluted in water (50 µl). The final DNA concentration of the purified product was 30 to 50 ng/µl.

The nucleotide sequence of the deletion region of the non-sporulating strains RS303 and RS310 is SEQ. ID NO.: 9. FIG. 2 also shows the sequence of the non-sporulating B. subtilis strain in the sigG gene region. The region deleted from the chromosome corresponds to region 1605063-1605739 in the sequence of the wild strain 168. From the 780 nucleotides of the region coding the sigG gene, 677 nucleotides have been removed by deletion. The region containing the cat gene (highlighted in grey) inserted at the deletion site corresponds to the nucleotides 973 to 1985 in the sequence of plasmid pC194 (Genbank acc. No. V01277). The SOE fragment made to perform the deletion contained a 21-base pairs long repeating sequence (bold) on the flanking regions of the cat region. The sequenced region starts from nucleotide 1603961 (↓) and the last sequenced nucleotide is 1606851 (↑). Primers SQ1 to SQ7 were used to sequence the RS303 strain. These primers were used to prepare the PCR products that were sequenced with the same primers. The sequence corresponding to (F primers) or complementary with (R primers) the primers used in ampling the PCR products is underlined. Primers A to F used in the SOE reactions are marked with a dashed line above the line. The starting codons of the sigG and cat genes are italicised, the end codon of the sigG gene is indicated with (*END) and the end codon of the cat gene with (*). Individual nucleotides that differ from the sequences of the gene bank are double-underlined. After deletion, the first 38 nucleotides and the last 65 nucleotides remain of the sigG gene. After the inserted cat gene, a 21-nucleotides long overlap region is repeated that has the same sequence as in the beginning of the sigG gene.

Differences to the published sequence of B. subtilis (Kunst et al., 1997) were found in the sequencing. The same sequence differences were obtained, when the sigG gene flanking regions of the wild strain 168 chromosome were sequenced. The differences in the sequence are marked to the sequence in the deletion region in FIG. 2. The homologous regions used in the integration were, however, identical with the sequence results of the wild strain B. subtilis 168.

Effect of sigG Gene Deletion on Sporulation

The effect of sigG deletion on sporulation was tested by growing sigG-deleted B. subtilis strain RS303 in a sporulation medium and by thermally treating the vegetative cells at +85° C. The stability of the deletion was monitored by growing RS303 under selection pressure (chloramphenicol 5 µg/ml SS broth) and without selection. After thermal treatment, the cells were plated on LB plates. Wild strain 168 was used as the control strain and treated in a corresponding manner. The broth of wild strain 168 had $2.1 \times 10^8$ spores per millilitre. RS303 did not produce any spores (Table 3). No spores were produced when growing RS303 cells without selection in SS broth. It can be concluded from this that the deletion of the sigG gene prevents the sporulation of the bacterium and that the sigG deletion is stable.

TABLE 3

Effect of sigG gene on sporulation

| Growth medium | B. subtilis 168 SS | RS303 SS + Cm | RS303 SS |
| --- | --- | --- | --- |
| Cells/ml | $3.9 \times 10^8$ | $1 \times 10^8$ | $8 \times 10^7$ |
| Spores/ml | $2.1 \times 10^8$ | 0 | 0 |

Constructing production plasmid, pRSH10, of β-lactamase

The secretion of a foreign protein to the growth medium was tested by inserting the β-lactamase gene of B. licheniformis 749/C bacterium into secretion vector pKTH141 (Lundström, 1985). In the vector, the secretion of the foreign protein is controlled by the α-amylase promoter and signal sequence of *B. amyloliquefaciens*. A desired fragment of a region coding the foreign protein can be inserted at the HindIII cloning site in the correct reading frame with the signal sequence, whereby the protein is secreted into the growth medium. The insertion was made as briefly described in the following: chromosomal DNA (Marmur, 1961) was isolated from the *Bacillus licheniformis* bacterium 749/C and used as a template in a PCR reaction. A 817-base pairs long PCR product was amplified from the template with PEL-141F (SEQ. ID NO.: 7) and PEN-141R (SEQ. ID NO.: 8) primers, the product containing an region coding a so-called small exopenicillinase corresponding to nucleotides 129 to 921 of the GenBank sequence V00093 (and amino acids 43 to 307 of the Swiss-Prot sequence P00808). The 100-μl PCR reaction mixture contained 10 ng template DNA, 0.3 μM primer, 0.2 mM dNTP, 10 μl enzyme manufacturer's buffer, 1.5 μl Expand enzyme (3.5 U/μl, Boehringer Mannheim). The PCR program comprised an initial 4-min heating at 94° C., then 28 times 40 s at 94° C., 20 s at 50° C., 1 min at 72° C., and finally 5 min at 72° C. The obtained PCR product was purified and inserted by means of the HindIII restriction sites added to the primers into pKTH141 to thus obtain production plasmid pRSH10. The region coding the β-lactamase of plasmid pRSH10 was sequenced and the sequence did not differ from the gene bank sequence. *B. subtilis* 168 and RS303 were transformed (Gryczan et al., 1978) with pRSH10 to obtain bacterial strains RS201 and RS310, respectively.

Effect of sigG Gene Deletion on Non-Sporulation and Stability of Deletion in β-Lactamase Overproduction Strain Transforming the non-sporulating, competent strain RS303 with production vector pRSH10 produced production strain RS310. The deletion of the sigG gene did not affect the competence of the bacterium. The sporulation of the new production strain and the stability of the sigG gene were monitored by growing the RS310 strain in a sporulation medium without chloramphenicol selection. The development of sporulation was further monitored during several growth cycles by reinoculating a 24-h growth into SS medium. A growth cycle refers herein to a 24-h growth that was inoculated 1:100 to a new sporulation medium. The sporulation was monitored during three growth cycles. Cells were taken from 1 to III growths for thermal treatment. After the thermal treatment, the cells were plated on LB plates or LB chloramphenicol plates.

In the growths, wild strain 168 produced $2.8 \times 10^8$ spores on average. The RS310 deletion strain did not produce any spores (Table 4). The fact that the non-sporulation remained in the RS310 strain when cells were grown in SS medium without chloramphenicol selection was considered an indicator of stability. The number of vegetative cells on the selective LB plates (chloramphenicol 5 μg/ml) also remained the same as that of the cells on the LB plates. The test showed that the construction of the deletion and the insertion of the cat gene are stable.

TABLE 4

Effect of sigG gene deletion on sporulation and stability of deletion in RS310 production strain

| | RS310 | | | *B. subtilis* 168 | |
|---|---|---|---|---|---|
| | Vegetative cells/ml | | Spores/ml | Cells/ml | Spores/ml |
| Growth | LB | LB + Cm | LB | LB | LB |
| I | $1.4 \times 10^8$ | $1.1 \times 10^8$ | 0 | $6 \times 10^8$ | $3.3 \times 10^8$ |
| II | $2.7 \times 10^8$ | $1.6 \times 10^8$ | 0 | $5.9 \times 10^8$ | $4.5 \times 10^8$ |
| III | $2.0 \times 10^8$ | $6.0 \times 10^7$ | 0 | $2.3 \times 10^8$ | $7.1 \times 10^7$ |

Table 5 shows the number of vegetative cells and sporulating cells in a second growth, in which the sporulation of the RS310 strain was monitored. This time, the number of vegetative cells was determined in RS310 growths in plates having a lower chloramphenicol content. By reducing the amount of chloramphenicol in the medium, the selection pressure was reduced, since with higher chloramphenicol concentration in plates, the growth of the bacterium was very slow. The colonies remained small and all vegetative cells were possibly not revealed. So as to obtain a more comparable result, the selection was reduced in the plates to 1 μg/ml of chloramphenicol. The number of vegetative cells in the chloramphenicol plates now remained the same as in the LB plates. Wild strain 168 used as the control strain produced $3.5 \times 10^8$ spores/ml on average. RS310 did not sporulate in the growths. Thus, these results, too, show well the effect of sigG gene deletion. The production strain is completely non-sporulating and very stable.

TABLE 5

Effect of sigG gene deletion on sporulation and stability of deletion in RS310 production strain

| | RS310 | | | *B. subtilis* 168 | |
|---|---|---|---|---|---|
| | Vegetative cells/ml | | Spores/ml | Cells/ml | Spores/ml |
| Growth | LB | LB + Chl | LB | LB | LB |
| I | $1.3 \times 10^8$ | $1.3 \times 10^8$ | 0 | $4 \times 10^8$ | $3.6 \times 10^8$ |
| II | $1.6 \times 10^8$ | $1.6 \times 10^8$ | 0 | $4.7 \times 10^8$ | $4.5 \times 10^8$ |
| III | $3.8 \times 10^8$ | $5.6 \times 10^8$ | 0 | $4.5 \times 10^8$ | $2.4 \times 10^8$ |

β-Lactamase Production of Non-Sporulating Strain

Figure 3:
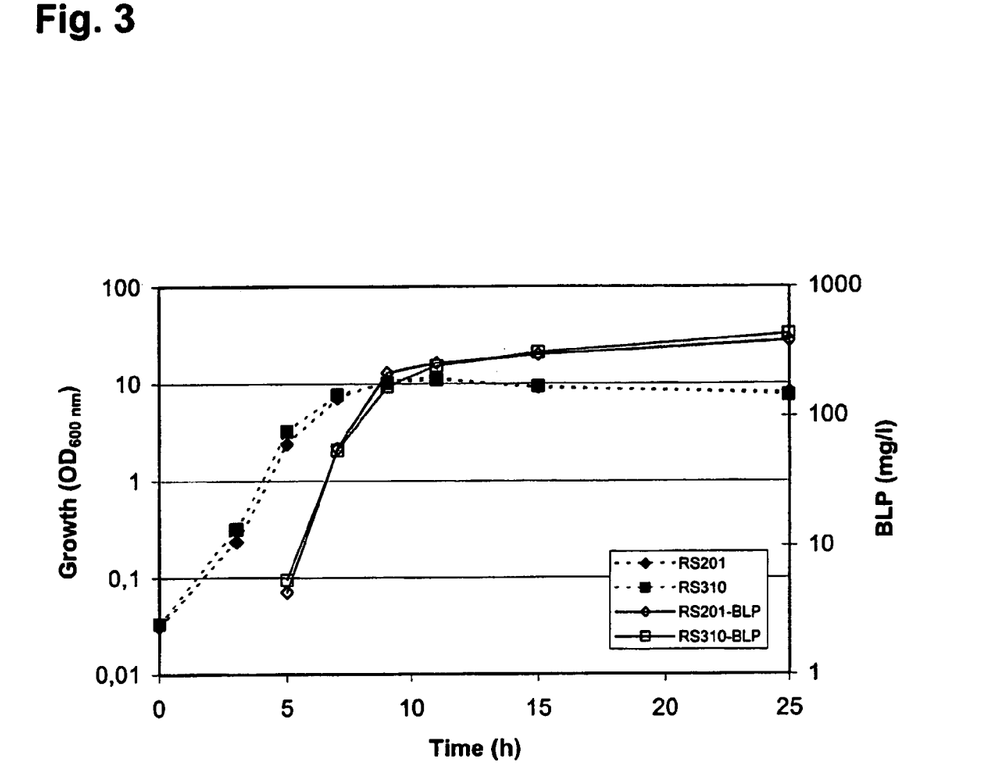
FIG. 3 shows the growth (-----) of a sporulating (RS201) and non-sporulating (RS310) *B. subtilis* strain and the production (━━━) of β-lactamase (BLP) in a 100-ml agitation growth.

The β-lactamase (BLP) production of the new non-sporulating bacterial strain, RS310, was compared with the production level of β-lactamase in wild strain 168 that was transformed with production plasmid pRSH10, i.e. in strain RS201. The β-lactamase production was monitored in a 100-ml agitation growth. The β-lactamase activity of the growth solution was measured by spectrophotometry according to the method developed by O'Callaghan et al. (1972) by using a chromogenic substrate, nitrocefin. The change in absorbance at 486 nm was converted into activity unit BU: 1 μmol degraded benzylpenicillin per hour, 30° C., using an experimentally determined coefficient 26.3. The activity units were, in turn, converted to μg β-lactamase/ml units by using the β-lactamase specific activity of 340 BU/βg protein (Simons et al., 1978). A concentrated LB medium with kanamycin 10 μg/ml as the selection was used as the growth medium. 0.1 ml of logarithmic-stage cells were inoculated into 100 ml of growth solution and the cells were grown in a 2-1 agitation bottle (+37°, 250 rpm). The growth was monitored for 25 hours by measuring the opacity ($OD_{600nm}$). The results are shown in FIG. 3. The bacterial strains RS310 and RS201 had a similar growth rate at the logarithmic growth stage and the highest $OD_{600nm}$ value was reached at 11 hours. The growth solutions of both strains then had approximately 250 µg/ml of β-lactamase. After 11 hours, the bacterial density started to decrease and at the end of the growth the $OD_{600nm}$ value of the RS310 strain was 7.6 and that of the RS201 strain 8.1. However, the amount of β-lactamase in the growth solution increased and was at the end of the growth 430 µg/ml for the new non-sporulating production strain RS310 and for the RS201 strain 380 µg/ml. In addition, the effect of sigG gene deletion on the profile of the proteins secreted into the growth broth was examined by means of an SDS-PAGE gel run, and no difference in the Coomassie-blue-coloured gels (15% acryl amide) was detected between the non-sporulating strain and the wild strain. On the basis of the obtained results, sigG gene deletion does not seem to disturb bacterial growth or the production of secreted proteins.

It is obvious to a person skilled in the art that while the technology advances, the basic idea of the invention can be implemented in many different ways. The invention and its embodiments are thus not restricted to the examples described above, but can vary within the scope of the claims.

REFERENCES

Biswas, I., A. Gruss, S. D. Ehrlich, and E. Maguin. 1993. High-efficiency gene inactivation and replacement system for gram-positive bacteria. J. Bacteriol. 175: 3628-3635.

Ehrlich, S. D. 1978. DNA cloning in *Bacillus subtilis*. Proc. Natl. Acad. Ssci. USA, 75: 1433-6.

Ferrari, E. and J. A. Hoch. 1989. Genetics. In: *Bacillus*, Biotechnology handbooks; v. 2. C. Harwood (ed.). Plenum Press, New York. A Division of Plenum Publishing corporation. New York.) pp. 57-72.

Fougler, D. and J. Errington (1989) The role of the sporulation gene spoIIIE in the regulation of prespore-specific gene expression in *Bacillus subtilis*. Mol. Microbiol. 3: 1247-1255.

Gryczan, T J., S. Contente, D. Dubnau. 1978. Characterization of *Staphylococcus aureus* plasmids introduced by transformation into *Bacillus subtilis*. J. Bact. 134: 318-329.

Haldenwang, W. 1995. The sigma factors of *Bacillus subtilis*. Microbiol. Rev. 59: 1-30.

Harwood, C. R. and S. M. Cutting (edit.), Molecular Biological Methods for *Bacillus*. 1991. Wiley-Interscience Publications.

Horinouchi S., and B. Weisblum. 1982. Nucleotide sequence and functional map of pC194, a plasmid that specifies inducible chloramphenicol resistance. J. Bacteriol. 150: 815-825.

Horton, Robert M., Henry D. Hunt, Steffan N. Ho, Jeffrey K Pullen and Larry R. Pease. 1989. Engineering hybrid genes without the use of restriction enzymes: gene splicing by overlap extension. Gene, 77: 61-68.

Illing N., Young M. & Errington J., 1990. Use of Integrational Plasmid Excision to Indentity Cellular Localization of Gene Expression during Sporulation in *Bacillus subtilis*. J. Bactriol. 172: 6937-6941.

Ishii, T., K Yoshida, G. Terai, Y. Fujita, and K. Nakai. 2001 DBTBS: a database of *Bacillus subtilis* promoters and transcription factors. Nucleic Acids Res. 29: 278-280.

Izui, K., J. B. K Nielsen, M. P. Gaulifield, and J. O. Lampen. 1980. Large exopenicillinase, initial extracellular form detected in growths of *Bacillus licheniformis*. Biochemistry 19: 1882-1886.

Karmazyn-Campbelli, C., Bonamy, C., Savelli, B., and Stragier, P. 1989. Tandem genes encoding σ-factors for consecutive steps of development in *Bacillus subtilis*. Genes Dev. 3: 150-157.

Khasanov, F. K., D. J. Zvingila, A. A. Zainullin, and A. A. Prozorov. 1992. Homologous recombination between plasmid and chromosomal DNA in *Bacillus subtilis* requires approximately 70 bp of homology. Mol. Gen. Genet. 234: 494-497.

Kunst F, Ogasawara N, Moszer I, Albertini A M, Alloni G, Azevedo V, Bertero M G, Bessieres P, Bolotin A, Borchert S, Borriss R, Boursier L, Brans A, Braun M, Brignell S C, Bron S, Brouillet S, Bruschi C V, Caldwell B, Capuano V, Carter N M, Choi S K, Codani J J, Connerton I F, Danchin A, et al. The complete genome sequence of the gram-positive bacterium *Bacillus subtilis*. Nature. 1997 Nov. 20; 390 249-256

Lundström, K. 1985. Expression of viral membrane protein genes in *Bacillus subtilis*. Ph.D. Thesis, University of Helsinki, 1985.

Marmur, J. 1961. A procedure for the isolation of deoxyribonucleic acid from microorganisms. J. Mol. Biol. 3: 208-218.

McPherson, M. J., and S. G. Møller. 2000. PCR: the Basics. BIOS Scientific Publishers, Oxford.

O'Callaghan C. H, A. Morris, S. M. Kirby, and A. H. Shingler. 1972. Novel method for detection of beta-lactamases by using a chromogenic cephalosporin substrate. Antimicrob. Agents Chemother. 1: 283-288.

Pedraza-Reyes M., Gutierrez-Corona F. & Nicholoson W L. 1994. Temporal regulation and forespore-specific expression of the spore photoproduct lyase gene by sigma-G RNA polymerase during *Bacillus subtilis* sporulation. J. Bacteriol. 176: 3983-9193.

Sambrook, J. and D. W. Russell. 2001. Molecular cloning, a laboratory manual. Cold Spring Harbour Laboratory Press, Cold Spring Harbour, New York.

Sambrook, J., Fritch, E. F. and Maniatis, T. 1989. Molecular cloning. A Laboratory Manual. Second edition. Cold Spring Harbor Laboratory Press, New York.

Simons K., M. Sarvas, H. Garoff, and A. Helenius. 1978. Membrane-bound and secreted forms of penicillinase from *Bacillus licheniformis*. J. Mol. Biol. 126: 673-690.

Stragier, P., and Losick, R. 1996. Molecular genetics of sporulation in *Bacillus subtilis*. Annu. Rev. Genet. 30: 297-341.

The invention claimed:

1. A non-sporulating *Bacillus subtilis* strain wherein a deletion region of at least 150 nucleotides is deleted from the sigG gene of the strain and an insertion region comprising a selection marker gene is inserted in the genome to replace the deletion region, wherein the strain comprises a first overlap region of at least 20 nucleotides upstream of the selection marker gene, and a second overlap region of at least 20 nucleotides downstream of the selection marker gene, and wherein the first and second overlap regions are homologous to each other, and wherein the genome of the strain comprises the sequence of SEQ ID NO: 9.

2. A method for preparing a non- sporulating *Bacillus subtilis* strain which comprises a sigG gene, the method comprising deleting a deletion region of at least 150 nucleotides from the sigG gene of the *Bacillus subtilis* strain to obtain said non-sporulating strain, wherein the sigG gene comprises two functional regions which code for amino acids 67 to 80 or 229 to 248, respectively, of the sigG protein, and wherein the method comprises deleting at least part of either of the two functional regions, wherein said step of deleting comprises
(a) preparing an insert construct which comprises a selection marker gene, flanked by an upstream recombination sequence and a downstream recombination sequence, wherein the first recombination region is homologous with a flanking region upstream of the gene region to be deleted, and the second recombination region is homologous with a flanking region downstream of the gene region to be deleted, and wherein the upstream recombination region, the selection marker gene, and the downstream recombination region are all approximately 1 kb in length, said insert construct being prepared by splicing by overlap extension (SOE) using primers that have at least approximately 20 nucleotides long overlap regions to produce an insert construct, wherein a first overlap region of at least 20 nucleotides immediately upstream of the selection marker gene is homologous with a second overlap region of at least 20 nucleotides immediately downstream of the selection marker gene, and (b) transforming *Bacillus subtilis* cells with the insert construct, whereby the insert construct is integrated into the chromosome as a result of a homologous double recombination; and (c) selecting transformed cells in which the insert construct has been integrated into their chromosomes whereby the deletion region has been deleted.

3. A method as claimed in claim 2, wherein the insert construct has a length of approximately 3 kb.

4. A method for producing a desired polypeptide product using a non-sporulating *Bacillus subtilis* strain, wherein a deletion region of at least 150 nucleotides has been deleted from its sigG gene, said method comprising transforming said strain with a polynucleotide construct encoding a recombinant polypeptide, expressing said polynucleotide construct, and recovering said recombinant polypeptide.

5. A method as claimed in claim 4, wherein the recombinant polypeptide is beta-lactamase.

* * * * *